United States Patent [19]

Campbell et al.

[11] Patent Number: 5,445,952
[45] Date of Patent: Aug. 29, 1995

[54] METHOD TO PRODUCE BIOTIN

[75] Inventors: John W. Campbell; Alex Cheung, both of Fort Collins; Christina K. Eddy, Loveland, all of Colo.

[73] Assignee: BASF Aktiengesellschaft, Ludwigshafen, Germany

[21] Appl. No.: 7,559

[22] Filed: Jan. 22, 1993

[51] Int. Cl.$^6$ ............... C12P 17/10; C12P 21/06; C12N 1/20; C07H 19/00

[52] U.S. Cl. ............... 435/121; 435/69.1; 435/119; 435/252.3; 435/252.33; 536/22.1; 536/23.1; 536/23.2; 536/23.4; 536/23.7

[58] Field of Search ............... 435/69.1, 119, 121, 435/252.3, 252.33, 320.1; 536/22.1, 23.1, 23.2, 23.4, 23.7

[56] References Cited

U.S. PATENT DOCUMENTS 5,110,731 5/1992 Fisher ............... 435/119

OTHER PUBLICATIONS

Eisenberg "Biosynthesis of . . ." *E. coli* and *Salmonella typhimurin* pp. 544–549 (1987).

Magnuson et al., "Cloning and nucleotide . . ." FEBS vol. 299, pp. 262–266 (Mar., 1992).
Sabatie et al. "Biotin formation by recombinant Strains . . ." J. of Biotechnology vol. 20, pp. 29–50 (1991).
Rawlings et al. "The gene encoding . . ." J. of Biological Chemistry vol. 267, No. 9 pp. 5751–5754 (Mar. 25, 1992).

*Primary Examiner*—Robert A. Wax
*Assistant Examiner*—Hyosuk Kim
*Attorney, Agent, or Firm*—Whyte Hirschboeck Dudek

[57] ABSTRACT

The present invention relates to a method to enhance a cell's ability to produce biotin precursors and/or biotin by deregulating at least one enzyme of the fatty acid biosynthetic pathway in the cell, preferably an enzyme that carries out an early step in the pathway. Preferably, the biotin biosynthetic pathway is also deregulated. The invention includes biotin-producing cells in which at least one enzyme of the fatty acid biosynthetic pathway is deregulated, preferably by transforming the cells with nucleic acid sequences encoding at least one of those enzymes; methods to produce such cells; and use of such cells to produce biotin.

3 Claims, 5 Drawing Sheets

METHOD TO PRODUCE BIOTIN

FIELD OF THE INVENTION

This invention relates to a method for improving biotin production by manipulating the fatty acid synthesis pathway to obtain increased production of biotin precursors and biotin.

BACKGROUND OF THE INVENTION

Biotin, or vitamin H, is an indispensable element in intermediary metabolism in many organisms since it is an essential factor of biotin-dependent carboxylases important in fatty acid synthesis, gluconeogenesis, and amino acid metabolism. Biotin is useful as a food supplement, a cosmetic additive, and a diagnostic reagent in biotin-avidin-based detection assays.

Most biotin for commercial use is currently produced by a complex chemical synthesis process. Although several investigators are attempting to synthesize biotin in commercial quantities using microbiological methods, the cost thus far has been prohibitive.

The biotin biosynthetic pathway converts pimelyl-CoA to biotin through a series of enzyme reactions. In microorganisms, such as *Escherichia coli* and Bacillus, most of these enzymes are encoded by genes contained on biotin gene clusters, or operons. Regulation of expression of these genes significantly influences biotin production. Wild type microorganisms, for example, produce only small amounts of the vitamin apparently because such microorganisms exert tight control over expression of the enzymes involved in biotin biosynthesis. Researchers have fed microorganisms pimelic acid and other biotin precursors in order to try to improve biotin production (see, for example, Ogata, pp. 390-394, 1970, *Methods in Enzymology*, vol. 17a; Izumi et al., pp. 231-256, in *Biotechnology of Vitamins, Pigments, and Growth Factors*, Elsevier Applied Science, E. J. Vandamme, ed.; U.S. Pat. No. 3,393,129, by Shibata et al., issued Jul. 16, 1968; and U.S. Pat. No. 4,563,426 by Yamada et al., issued Jan. 7, 1986). In addition, a variety of recombinant DNA techniques have been employed to try to improve microbial biotin production including (a) transformation of genes encoding enzymes involved in the biotin biosynthetic pathway (i.e., biotin biosynthetic pathway genes) into microorganisms (see, for example, GB Publication No. 2,216,530, by Pearson et al., published Oct. 11, 1989; U.S. Pat. No. 5,110,731, by Fisher, issued May 5, 1992); (b) feeding of biotin precursors, such as pimelic acid, to such transformed microorganisms (see, for example, European Patent Publication No. 375,525, by Gloeckler et al., published Jun 27, 1990; Sabatie et al., pp. 29-50, 1991, *Journal of Biotechnology*, vol. 20; Ohsawa et al., pp. 39-48, 1989, *Gene*, vol. 80; and Ohsawa et al., pp. 121-124, 1992, *J. Ferment. Bioeng.*, vol. 73); and (c) isolation of derepressed mutants for biotin biosynthesis (see, for example Japanese Patent Publication No. 62,155,081, assigned to Shiseido KK, published Jul. 10, 1987; Japanese Patent Publication No. 61,202,686, assigned to Shiseido KK, published Sep. 8, 1986; and Japanese Patent Publication No. 61,149,091, assigned to Nippon Soda KK, published Jul. 7, 1986). These attempts have resulted in some increased biotin production; however, in each case, the amount of biotin produced using such methods is substantially lower than that required for a commercially viable process.

While it is known that pimelyl-CoA is a precursor of biotin and that feeding of pimelic acid to microorganisms can improve biotin production, the intracellular source of pimelic acid and its derivatives (e.g., pimelyl-CoA) was not recognized until the present invention. Several investigators have speculated about the source of pimelic acid. For example, Ohsugi et al., pp. 343-352, 1988, *J. Nutr. Vitaminol.*, vol. 34, and pp. 253-263, 1985, *J. Nutr. Vitaminol.*, vol. 31, discussed the possibility that pimelic acid might be formed from long chain fatty acids, such as oleic, linoleic, and linolenic acids, via a degradation process. Eisenberg, pp. 544-550, 1987, *Escherichia coli and Salmonella typhimurium Cellular and Molecular Biology* (Neidhardt, F. C. et al., eds., American Society of Microbiology, Washington, D.C.) speculated that pimelyl-CoA might be a product derived from fatty acid synthesis and degradation steps, based on an isotopic study conducted by Lezius et al. (pp. 510-525, 1963, *Biochem. Z.*, vol. 336) in *Achromobacter*, a study which also led Lezius et al. to conclude incorrectly that biotin production involves a condensation reaction between pimelyl-CoA and cysteine. Eisenberg further speculated that, even if pimelyl-CoA were to be produced using the fatty acid pathway, a mechanism would be required to either add or subtract a carbon from a fatty acid chain (which has an even number of carbons) to form pimelate (which has seven carbons). Eisenberg also suggested that biotin and lipoic acid are very similar and that the process to produce them probably involves octanoic acid as an intermediate. Since octanoic acid has eight carbons, such a process would require removal of a carbon atom to form pimelate. Eisenberg further suggests that the octanoic acid may be produced de novo or by degradation of long chain fatty acids.

The fatty acid biosynthetic pathway converts acetyl coenzyme A (acetyl-CoA) to short-chain and long-chain fatty acids through a series of enzymatic reactions (see, for example, the following review articles: Vanden Boom et al., pp. 317-343, 1989, *Annu. Rev. Microbiol.*, vol. 43; McCarthy et al., pp. 60-63, 1984, *Trends Biochem. Sci.*; Stumpf et al., pp. 173-176, 1981, *Trends Biochem. Sci.*; Vagelos, pp 100-140, 1974, "*MTP International Review of Science, Biochemistry of Lipid*", T. W. Goodwin, ed., Butterworth, London). Although fatty acid synthesis is essentially ubiquitous throughout nature and the general mechanism (i.e., reactions) by which fatty acids are synthesized is similar, the structural form of the enzymes involved in the pathway differs significantly between organisms. The different structures are grouped into two types, which are called Type I fatty acid synthesis (FAS) and Type II FAS. Plants and most bacteria exhibit Type II FAS in which essentially each reaction along the pathway is carried out by a separate enzyme. In contrast, other organisms (e.g., animals and fungi) exhibit Type I FAS in which the reactions are typically carried out by multifunctional proteins that exhibit more than one enzymatic activity. Substantial sequence and functional homologies can be found between the discrete Type II FAS enzymes and corresponding regions on Type I FAS multifunctional proteins.

FIGS. 1 and 2 illustrate the fatty acid synthesis pathway as it is currently known in *Escherichia coli*. Each of the enzymes involved in this pathway has been identified and the current belief of how the enzymes effect synthesis of fatty acids follows: The first step of fatty acid biosynthesis is the conversion of acetyl-CoA to malonyl coenzyme A (malonyl-CoA). This reaction is catalyzed by the enzyme complex acetyl-CoA carboxylase (ACC) which includes 4 dissociable subunits: biotin carboxylase (BC), which is encoded by the accC gene; biotin carboxyl-carrier protein (BCCP), which is encoded by the accB gene (formerly known as the fabE gene); and carboxyl transferase (CT), which consists of two heterologous subunits encoded by the accA and accD genes. Biotin is an essential co-factor of acetyl-CoA carboxylase.

Malonyl-CoA is then converted to malonyl-acyl carrier protein (malonyl-ACP) by malonyl coenzyme A-acyl carrier protein transacylase, which is encoded by the fabD gene. The acyl carrier protein (ACP) is encoded by the acpP gene. A 3-ketoacyl-acyl carrier protein synthetase subsequently combines malonyl-ACP with either acetyl-ACP or acetyl-CoA (depending on the enzyme) to form acetoacetyl-ACP and carbon dioxide. At least two enzymes can perform this condensation step in $Escherichia\ coli$. 3-ketoacyl-acyl carrier protein synthetase III (KAS III), encoded by the fabH gene, can combine acetyl-CoA with malonyl-ACP to form acetoacetyl-ACP. KAS III also has an acetyl-CoA:ACP transacylase activity. In contrast, 3-ketoacyl-acyl carrier protein synthetase I (KAS I), encoded by the fabB gene, can combine acetyl-ACP and malonyl-ACP to form acetoacetyl-ACP. KAS I also exhibits a decarboxylase activity capable of converting malonyl-ACP to acetyl-ACP.

Acetoacetyl-ACP is further elongated, two carbons at a time, by a series of reactions in which malonyl-ACP is added to the chain and carbon dioxide is removed. After each condensation step, the growing fatty acid is reduced by 3-ketoacyl ACP reductase, dehydrated by 3-hydroxyacyl ACP dehydratase, and reduced by enoyl ACP reductase. Another step in the production of unsaturated fatty acids is mediated by 3-hydroxydecanoyl thioester dehydratase (encoded by the fabA gene). This enzyme can convert 3-hydroxydecanoyl-ACP to 2-decanoyl-ACP which the enzyme can then isomerize to form 3-decanoyl-ACP. Yet another enzyme, 3-ketoacyl-ACP synthetase II (encoded by the fabF gene) converts palmitoleoyl-ACP to cis-vaccenoyl-ACP.

Several of the genes encoding enzymes of the fatty acid synthesis pathway have recently been isolated from $Escherichia\ coli$. These genes include accA (see, for example, Li et al., pp. 16841–16847, 1992, $J.\ Biol.\ Chem$, vol. 267); accB (see, for example, Li et al., pp. 855–863, 1992, $J.\ Biol.\ Chem$, vol. 267); accC (see, for example, Li et al., pp. 855–863, 1992, $J.\ Biol.\ Chem$, vol. 267); accD (see, for example, Li et al., pp. 5755–5757, 1992, $J.\ Bacteriol.$, vol. 174); fabA (see, for example, Cronan et al., pp. 4641–4646, 1988, $J.\ Biol.\ Chem.$, vol. 263); fabB (see, for example, de Mendoza et al., pp. 2098–2101, 1983, $J.\ Biol.\ Chem.$, vol. 258); fabD (see, for example, Magnuson et al., pp. 262–266, 1992, $FEBS\ Letters$, vol. 299; and Verwoert et al., pp. 2851–2857, 1992, $J.\ Bacteriol$, vol. 174); fabG (see, for example, Rawlings et al., 5751–5754, 1992, $J.\ Biol.\ Chem.$, vol. 267); fabH (see, for example, Tsay et al., pp. 6807–6814, 1992, $J.\ Biol.\ Chem.$, vol. 267); and acpP (see, for example, Rawlings et al., ibid.). The accB and accC genes are located adjacent to each other on the $Escherichia\ coli$ chromosome and are co-transcribed (see, for example, Li et al., pp. 855–863, 1992, $J.\ Biol.\ Chem$, vol. 267). The fabD, fabF, fabG, fabH, and acpP genes are also clustered on the $Escherichia\ coli$ chromosome (see, for example, Rawlings et al., ibid.; Tsay et al., ibid.).

Two antibiotics, thiolactomycin and cerulenin, have been used to distinguish the enzymatic activities of 3-ketoacyl-ACP synthetases I, II, and III. Thiolactomycin (TLM) selectively inhibits 3-ketoacyl-ACP synthetase I, II and III, possibly by blocking the malonyl-ACP binding sites on the enzymes. Cerulenin is known to inhibit 3-ketoacyl-ACP synthetases I and II. Amplification of the fabB gene, encoding 3-ketoacyl-ACP synthetase I, in an $Escherichia\ coli$ microorganism, confers TLM resistance to the microorganism (see, for example, Tsay et al., pp. 508–513, 1992, $J.\ Bacteriol.$, vol. 174).

Attempts to analyze the enzyme components of the fatty acid synthesis pathway have included producing null and temperature sensitive mutants to be used in a variety of growth studies. Two null mutants have been isolated, namely fabA$^-$ and fabF$^-$ mutants. A series of temperature sensitive mutants have been isolated including fabD$^{ts}$, fabE$^{ts}$ (i.e., accB$^{ts}$), fabA$^{ts}$, fabB$^{ts}$, and fabF$^{ts}$fabB$^{ts}$.

Efforts to increase biotin production by genetic manipulation of components of the biotin biosynthetic pathway have been hampered by a lack of understanding of how carbon flows into the biotin biosynthetic pathway. Increasing pimelic acid by exogenous supplementation of the growth medium has resulted in at least some increased biotin production. There remains, however, a need to improve cellular biotin production by increasing endogenous sources of biotin precursors, for example, by engineering cells to bring more carbon into the biotin biosynthetic pathway in order to overproduce biotin precursors such as pimelyl-CoA.

SUMMARY OF THE INVENTION

The present invention relates to the surprising discovery that pimelic acid, or a derivative thereof (e.g., pimelyl-CoA or pimelyl-ACP), is produced directly from early precursors in the fatty acid biosynthetic pathway (e.g., malonyl-CoA and/or malonyl-ACP). As such, the present invention includes a method to enhance a cell's ability to produce biotin precursors and/or biotin by deregulating at least one enzyme of the fatty acid biosynthetic pathway in the cell, and particularly at least one of the early steps in that pathway. The invention also includes cells in which at least one such enzyme has been deregulated. Preferred enzymes to deregulate include those enzymes which, through their deregulation, enhance the flow of carbon through the fatty acid biosynthetic pathway in such a way as to augment biotin precursor (and thus ultimately biotin) production. As such, preferred enzymes to deregulate include, but are not limited to, malonyl-CoA-ACP transacylase (MTA), or a functional equivalent thereof; at least one TIM-sensitive 3-ketoacyl-acyl carrier protein synthetase (KAS) that, when deregulated, leads to enhanced production of biotin precursors by a cell, or a functional equivalent of such a KAS; any additional TLM-sensitive enzymes or functional equivalents thereof that enhance biotin precursor production by a cell; at least one subunit of the acetyl coenzyme A carboxylase (ACC) complex, or a functional equivalent thereof; or mixtures thereof. In one embodiment of the present invention, at least one additional enzyme of the cell's fatty acid synthesis pathway is deregulated. In a preferred embodiment, the biotin biosynthetic pathway of the cell is also deregulated. Preferred cells of the present invention are bacteria, yeast, and other fungi. More preferred cells are of the genus Escherichia, Bacillus, Pseudomonas, Salmonella, Corynebacterium, or Saccharomyces. A particularly preferred species is *Escherichia coli*.

In accordance with the present invention, enzymes of the fatty acid or biotin biosynthetic pathways can be deregulated in a variety of ways including, but not limited to, substantially derepressing synthesis of the enzyme, substantially increasing the specific activity of the enzyme, substantially reducing an activity competitive with the enzyme (i.e., substantially decreasing the activity of any competing enzyme), and/or amplifying the copy number of a nucleic acid sequence encoding the enzyme. A preferred method for deregulating an enzyme is to transform a cell with a nucleic acid sequence encoding the enzyme. Such a cell preferably is transformed with a recombinant molecule in which the nucleic acid sequence is operatively linked to a transcription control sequence that is functional in that cell. Preferred transcription control sequences for use in *Escherichia coli* are bacteriophage T7, bacteriophage lambda, and tac transcription control sequences. Preferred nucleic acids with which to transform cells include MTA nucleic acid sequences; TLM-sensitive enzyme nucleic acid sequences, preferably KAS nucleic acid sequences; ACC subunit nucleic acid sequences; functional equivalents thereof; and mixtures thereof.

When cultured in an effective medium, cells of the present invention preferably are capable of producing at least about 10 milligrams (mg), more preferably at least about 50 mg, and even more preferably at least about 200 mg, of biotin per liter of medium per day (i.e., within about 24 hours). Preferred cells of the present invention are capable of converting at least about 90 percent of biotin vitamers to true biotin. A particularly preferred cell is capable of producing essentially about 100 percent of its total biotin as true biotin.

DETAILED DESCRIPTION OF THE INVENTION

The present invention is directed toward a method for improving microbial production of biotin by increasing the amount of carbon that flows into the biotin biosynthetic pathway. The present invention is partially predicated on the surprising discovery that deregulation of at least one early step of the fatty acid biosynthetic pathway leads to increased production of biotin by cells capable of producing biotin. Moreover, the inventors have discovered that pimelic acid, or a derivative thereof (e.g., pimelyl-CoA, pimelyl-ACP), can be produced directly from malonyl-CoA and/or malonyl-ACP that the cell has synthesized de novo. For example, the inventors have shown that feeding of isotopic-labeled carbonate (e.g., $[^{13}C]$—$CaCO_3$) to cells causes the cells to produce biotin having the isotopic-label in the appropriate position to suggest that the isotopic-label was derived from malonyl-CoA that had been produced by adding the isotopic-labeled carbonate to acetyl-CoA according to the reaction carried out by the ACC complex of the fatty acid biosynthetic pathway. The inventors have also obtained genetic and antibiotic data that support the present invention. As such, one aspect of the present invention is a method to increase cellular biotin production by increasing the amount of carbon that flows through the fatty acid biosynthetic pathway, and particularly through the initial steps of the pathway, in order to augment production of biotin precursors (e.g., pimelic acid, pimelyl-CoA and/or pimelyl-ACP).

Figure 1:
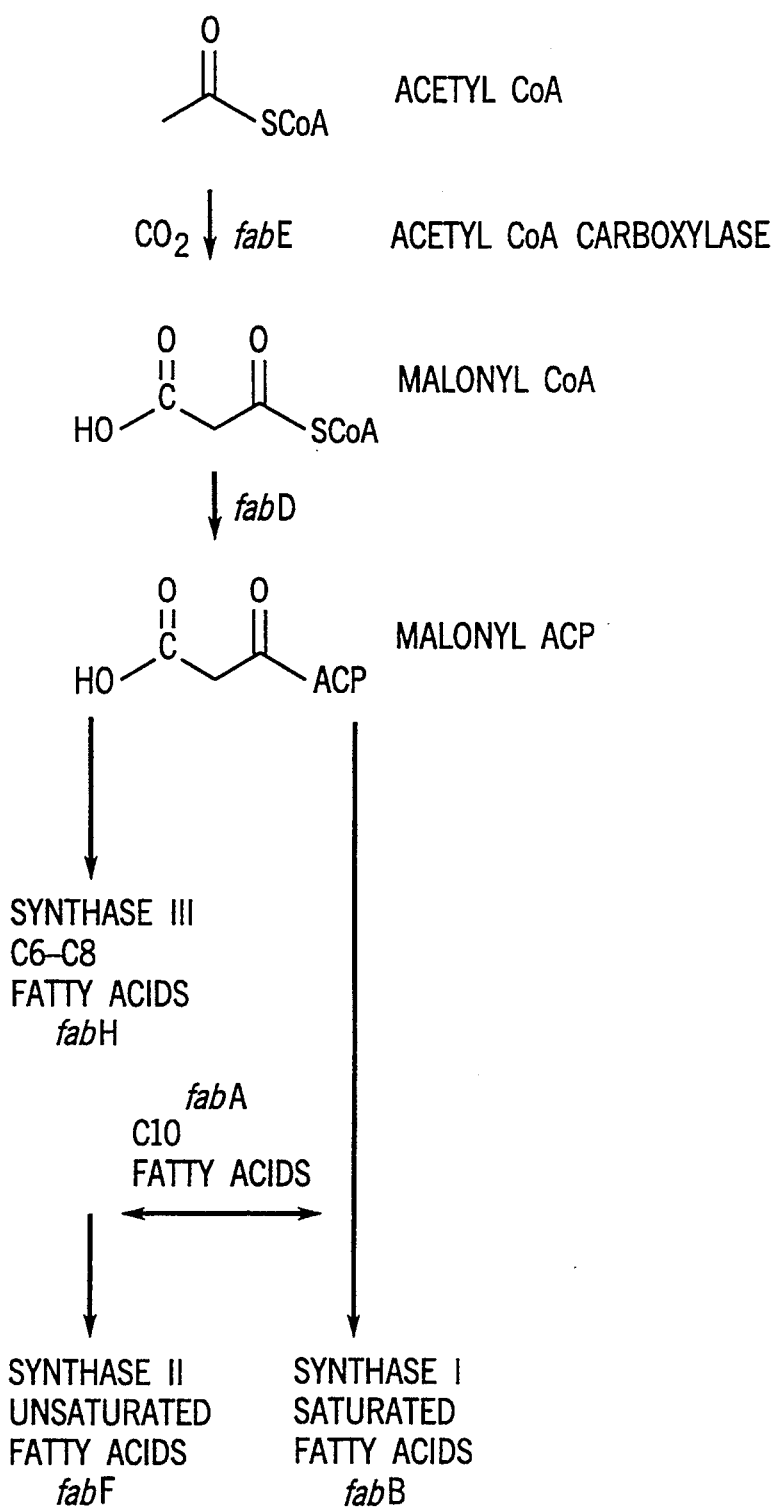
FIG. 1 is a schematic of the fatty acid biosynthetic pathway in *Escherichia coli*.
Figure 2:
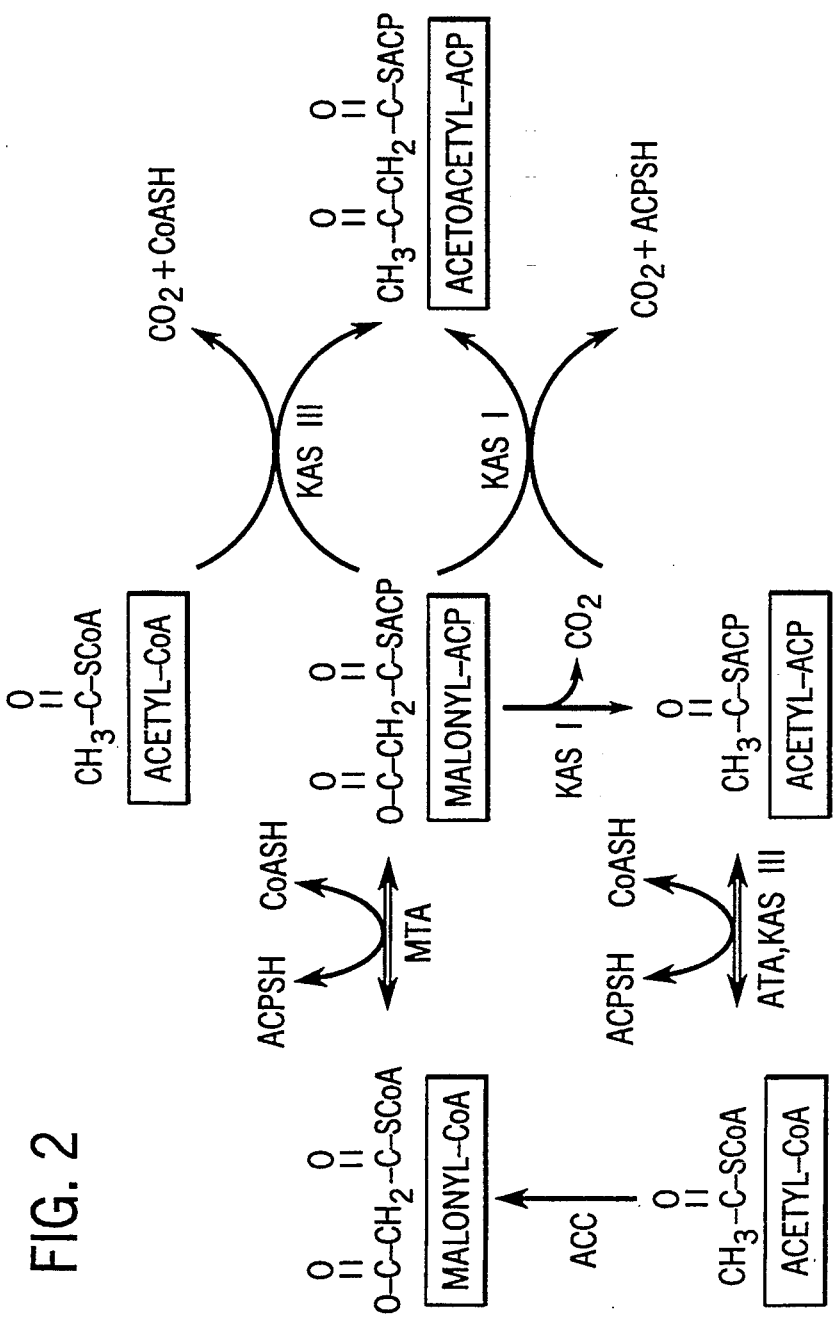
FIG. 2 is a schematic detailing the initial stages of the fatty acid biosynthetic pathway in *Escherichia coli*, taken from Tsay et al., ibid.
Figure 3:
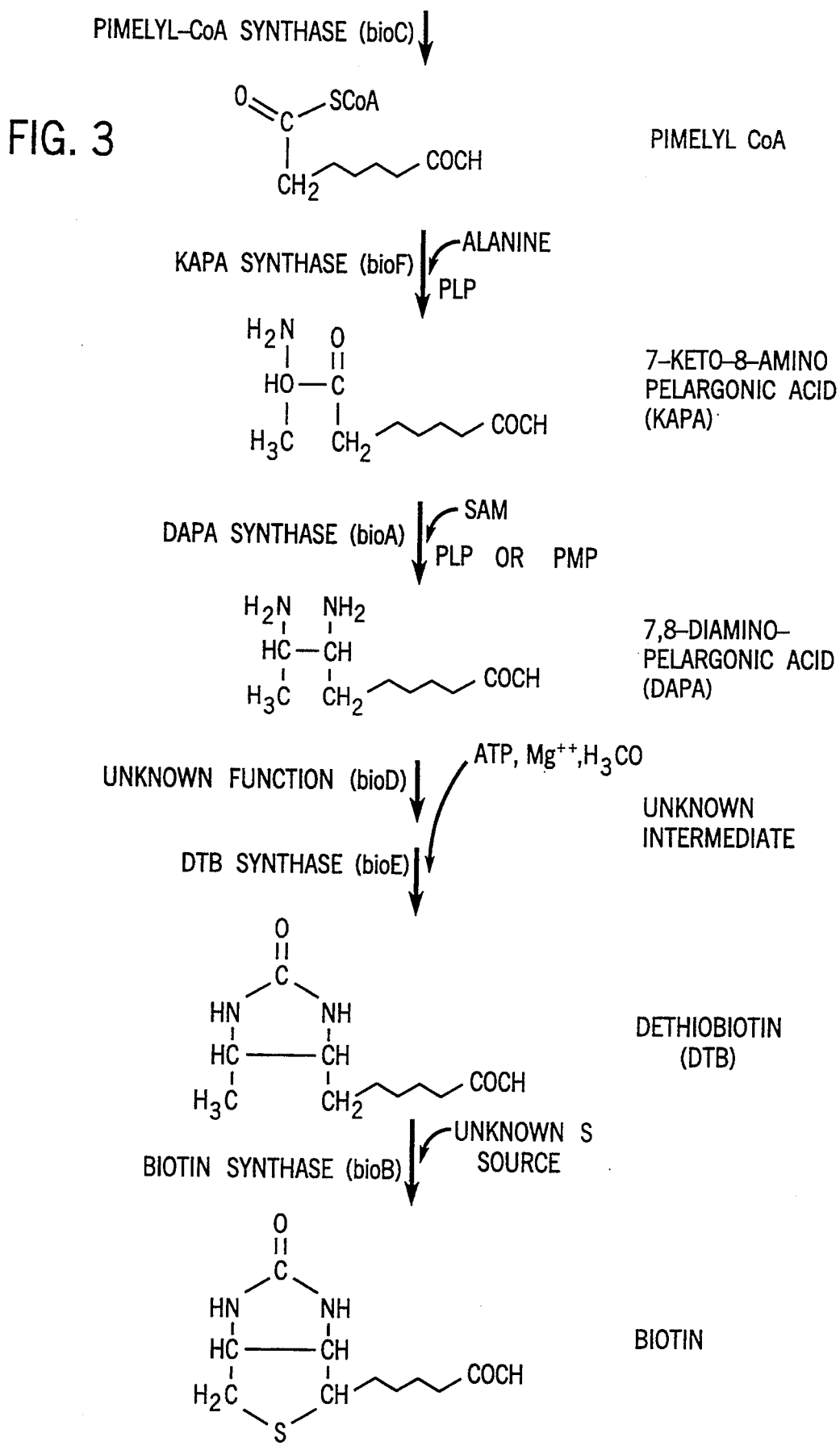
FIG. 3 is a schematic of the biotin biosynthetic pathway in *Escherichia coli*.

While not being bound by theory, the inventors believe that cells may produce the biotin precursor pimelyl-CoA, or a close derivative thereof, in the following manner: Two malonyl-ACP moieties can be combined to produce $\beta$-ketoglutaryl-ACP and carbon dioxide. The keto group of $\beta$-ketoglutaryl-ACP can then be reduced to form glutaryl-ACP in a manner analogous to that by which the fatty acid biosynthetic pathway reduces fatty acid intermediates. Glutaryl-ACP can then be combined with another malonyl-ACP moiety to produce $\beta$-ketopimelyl-ACP and carbon dioxide, the $\beta$-ketopimelyl-ACP subsequently being reduced to pimelyl-ACP. Pimelyl-ACP can then be converted to pimelyl-CoA, which is subsequently converted to biotin according to the biotin biosynthetic pathway in FIG. 3 and as disclosed in co-pending U.S. patent application Ser. No. 08/001,063, by Eddy et al., filed Jan. 6, 1993, Attorney File No. 2096-58, which is incorporated herein by reference in its entirety. The inventors have also discovered that biotin production is sensitive to TLM, which inhibits 3-ketoacyl-ACP synthetases, possibly by blocking the malonyl-ACP binding sites on the enzyme. As such, it is believed that a 3-ketoacyl-ACP synthetase is likely to be involved in at least one of the reactions converting malonyl-CoA to pimelyl-CoA.

Wild-type cells control the amounts and specific activities of enzymes involved in a number of biosynthetic pathways, including the fatty acid and biotin biosynthetic pathways so as not to overproduce compounds, such as fatty acids or vitamins. According to the present invention, biotin production in a cell surprisingly can be increased by deregulating at least one enzyme involved in fatty acid synthesis, particularly in the early stages of the pathway, in order to augment carbon flow through the portion of the fatty acid biosynthetic pathway leading to enhanced biotin precursor production. As used herein, a "deregulated enzyme" is an enzyme that is able to convert more substrate to product because, for example, there is an increased amount of the enzyme present in the cell, the enzyme has a higher specific activity, an activity (i.e., an enzyme that competes with the desired enzyme for substrate) is substantially reduced, or combinations thereof. It should be noted that "deregulated enzymes" include nonenzymatic proteins (usually subunits, e.g., biotin carboxyl-carrier protein) that influence the enzymatic activity of an enzyme complex containing or interacting with that protein.

The amount of an enzyme present in the cell can be increased in a variety of ways including, but not limited to, substantially derepressing synthesis of the enzyme, amplifying the copy number of a nucleic acid sequence encoding the enzyme, and combinations thereof.

As used herein, "substantially derepressing synthesis of the enzyme" refers to production of greater amounts of the enzyme than are normally produced by wild-type cells such that the amount and/or rate of substrate-to-product conversion is higher than in wild-type cells (i.e., there is enhanced conversion of substrate to product). Derepression of enzyme synthesis can be accomplished in a variety of ways, including interfering with the regulatory controls that a microorganism normally exerts over transcription and/or translation of the gene encoding the enzyme and increasing the stability of the messenger RNA (mRNA) corresponding to the enzyme. For example, synthesis of an enzyme which is normally subject to repression, may be increased by at least partially inactivating the respective repressor and/or modifying the operator sequence to reduce the ability of the repressor to bind to it. Modification of transcription (e.g., promoter) and/or translation (e.g., Shine Delgarno sequence) control signals (e.g., initiation, elongation, and/or termination signals) can also enhance both the rate and amount of enzyme production. Methods to derepress enzyme synthesis include random or targeted mutagenesis which can be accomplished, for example, by traditional mutation-selection or recombinant DNA techniques.

As used herein, amplifying the copy number of a nucleic acid sequence in a cell can be accomplished either by increasing the copy number of the nucleic acid sequence in the cell's genome or by introducing additional copies of the nucleic acid sequence into the cell by transformation. Copy number amplification is conducted in a manner such that greater amounts of enzyme are produced, leading to enhanced conversion of substrate to product. For example, recombinant molecules containing nucleic acids of the present invention can be transformed into cells to enhance enzyme synthesis. Transformation can be accomplished using any process by which nucleic acid sequences are inserted into a cell. Transformation techniques include, but are not limited to, transfection, electroporation, microinjection, lipofection, adsorption, and protoplast fusion. After transformation, the cell can produce multiple copies of the nucleic acid sequence, which can either remain on extrachromosomal vectors or be integrated into the host genome. Prior to transformation, the nucleic acid sequence on the recombinant molecule can be manipulated to encode an enzyme having a higher specific activity.

As used herein, "substantially increasing the specific activity of an enzyme" refers to modifications of a wild-type enzyme to obtain a deregulated enzyme which is able to convert substantially more substrate to product than essentially the same amount of the wild-type enzyme is able to convert. The specific activity of an enzyme can be increased in a variety of ways including, but not limited to, modifying the catalytic rate of the enzyme, reducing susceptibility of the enzyme to feedback inhibition, and combinations thereof. Methods to increase the specific activity of an enzyme include random or targeted mutagenesis which can be accomplished, for example, by traditional mutation-selection and/or recombinant DNA techniques.

As used herein, "substantially reducing an activity competitive with that of the enzyme" refers to modifications made to competitive enzymes such that the competitive enzymes, or activities, are no longer able to convert as much substrate to product, thereby allowing more of the substrate to be converted by the desired enzyme to the desired product. Methods to reduce competitive enzymes (i.e., activities) include random or targeted mutagenesis of such competitive enzymes which can be accomplished, for example, by traditional mutation-selection and/or recombinant DNA techniques.

One embodiment of the present invention is a biotin-producing cell (i.e., a cell capable of producing biotin) in which at least one of the following enzymes of the fatty acid biosynthetic pathway is deregulated: malonyl-CoA-ACP transacylase (MTA), or a functional equivalent thereof; a TLM-sensitive enzyme, preferably a 3-ketoacyl-acyl carrier protein synthetase (KAS) or a functional equivalent thereof, the deregulation of which leads to enhanced biotin precursor production by the cell,; and at least one subunit of the acetyl-Co A carboxylase (ACC) complex, or a functional equivalent thereof, such that the cell is capable of enhanced biotin or biotin precursor production. MTA, KAS, and at least one ACC subunit are preferred targets for deregulation since these enzymes are thought to carry out reactions in the pathway by which biotin precursors (e.g., pimelyl-CoA) are produced.

As used herein, a cell capable of enhanced biotin or biotin precursor production is any cell that is capable of producing detectably more biotin or biotin precursors than a parental cell in which the fatty acid biosynthetic pathway has not been deregulated. Total biotin, true biotin, and biotin vitamer production levels can be measured in a variety of ways known to one skilled in the art including, but not limited to, microbiological, chromatographic, and chemical assays. One microbiological assay which distinguishes total biotin and true biotin is disclosed in Ogata et al., pp. 889-894, 1965, *Agr. Biol. Chem.*, Vol. 29. Total biotin includes the entire spectrum of true biotin and biotin vitamer molecules that can be utilized by *Saccharomyces cerevisiae*; true biotin supports the growth of *Lactobacillus arabinosus*; and biotin vitamers include those vitamers that are utilized by *Saccharomyces cerevisiae* but that do not support the growth of *Lactobacillus arabinosus*.

As used herein, parental cells are the cells from which cells of the present invention are derived. Parental cells can be wild-type or mutant cells, and can be recombinant (i.e., transformed) or nonrecombinant.

Cells of the present invention can be of any species capable of producing fatty acids and biotin, including bacterial, yeast, other fungal, insect, animal, and plant cells. Preferred cells of the present invention are bacterial, yeast, and other fungal cells. More preferred cells are of the genus Escherichia, Bacillus, Pseudomonas, Salmonella, Corynebacterium, and Saccharomyces. Even more preferred cells are of the species *Escherichia coli*.

As used herein, a functional equivalent of any given enzyme is an enzyme that has a substantially similar biological activity as the given enzyme. A functional equivalent of a deregulated enzyme is also deregulated. A functionally equivalent enzyme can, but need not, share significant amino acid sequence homology with the given enzyme. A functionally equivalent enzyme can be a modified version of the given enzyme in which amino acids have been deleted. (e.g., a truncated version of the enzyme), inserted, inverted, substituted and/or derivatized (e.g., glycosylated, phosphorylated, acetylated) such that the modified enzyme has a biological function substantially similar to that of the given enzyme. Modifications can be accomplished by techniques known in the art including, but not limited to, direct modifications to the protein or modifications to the gene encoding the protein using, for example, classic or recombinant DNA techniques to effect random or targeted mutagenesis. Functionally equivalent enzymes can be selected using assays set up to measure enzyme activity.

It is within the scope of the present invention to use a variety of methods, such as those described above, to deregulate an enzyme. A preferred method to obtain a cell containing a deregulated enzyme is to transform the cell with a nucleic acid sequence encoding the enzyme or with a functionally equivalent nucleic acid sequence. As used herein, a "functional equivalent" of a particular nucleic acid sequence is a nucleic acid sequence that encodes a protein having substantially the same biological function as the protein encoded by the particular gene.

Functionally equivalent nucleic acid sequences can include nucleic acid sequences containing modifications, such as nucleotide deletions, additions, inversions, and/or substitutions that do not substantially interfere with the nucleic acid sequence's ability to encode a biologically active enzyme. That is, functionally equivalent nucleic acid sequences of the present invention encode enzymes having a biological activity similar to their natural counterparts. Functionally equivalent eukaryotic nucleic acid sequences can also include intervening and/or untranslated sequences surrounding and/or within the coding regions of the nucleic acid sequences.

A functionally equivalent nucleic acid sequence can be obtained using methods known to those skilled in the art (see, for example, Sambrook et al., *Molecular Cloning: A Laboratory Manual*, Cold Spring Harbor Labs Press, 1989, which is incorporated herein by reference in its entirety.). For example, nucleic acid sequences can be modified using a variety of techniques including, but not limited to, classic mutagenesis techniques and recombinant DNA techniques, such as site-directed mutagenesis, chemical treatment of a nucleic acid to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid sequences, and combinations thereof. Functionally equivalent nucleic acids can be selected from a mixture of modified nucleic acid sequences by screening for the function of the protein encoded by the nucleic acid sequence. A number of screening techniques are known to those skilled in the art including, but not limited to, complementation assays, binding assays, and enzyme assays. In one embodiment, a nucleic acid sequence obtained from any source that is functionally equivalent to the *Escherichia coli* fabD gene can be selected by its ability to complement an *Escherichia coli* strain that lacks a functional fabD gene. For example, a nucleic acid sequence functionally equivalent to the *Escherichia coli* fabD gene from any bacterial, yeast or other fungal strain can be selected by transforming a microorganism (preferably *Escherichia coli*) that lacks a functional fabD gene with a genomic or cDNA expression library prepared from that strain in which the genes are capable of being expressed in *Escherichia coli*, isolating transformed microorganisms that grow in the absence of fatty acids, and isolating nucleic acid sequences that enable such a microorganism to grow in the absence of fatty acids.

Functionally equivalent enzymes and nucleic acid sequences can be derived from any source. For example, functionally equivalent enzymes and nucleic acid sequences involved in fatty acid biosynthesis can be derived from any fatty acid-producing cell. Similarly, functionally equivalent enzymes and nucleic acid sequences involved in biotin biosynthesis can be derived from any biotin-producing cell. Functionally equivalent enzymes can include distinct enzymes or portions of multifunctional enzymes having essentially the same activity. Similarly functionally equivalent nucleic acid sequences can include coding regions for one or more enzymatic functions. For example, yeast, rat, chicken, and bacterial acetyl-CoA complexes are known to be functionally equivalent even though yeast, rat, and chicken acetyl-CoA complexes, unlike bacterial complexes, are part of a multifunctional protein (see, for example, Vanden Boom et al., ibid.).

Preferred sources of nucleic acid sequences of the present invention are bacterial, yeast, and other fungal cells, although it is within the scope of the invention to isolate nucleic acid sequences from any fatty acid-producing cell. More preferred sources are Escherichia, Bacillus, Pseudomonas, Salmonella, Corynebacterium, or Saccharomyces, with *Escherichia coli, Bacillus sphaericus,* and *Bacillus subtilis* being more preferred, and with *Escherichia coli* being even more preferred.

One embodiment of the present invention is a biotin-producing cell containing a deregulated MTA or functional equivalent thereof. Although it is within the scope of the present invention to deregulate MTA in a variety of ways, preferably deregulation of MTA is accomplished by transforming the cell with an MTA nucleic acid sequence or functional equivalent thereof in order to increase the copy number of nucleic acid sequences encoding MTA or a functional equivalent thereof. As used herein, a "MTA nucleic acid sequence or functional equivalent thereof" is any nucleic acid sequence encoding an enzyme having a biological function similar to MTA. A preferred MTA nucleic acid sequence is an *Escherichia coli* fabD gene, which encodes MTA in *Escherichia coli*. As used herein, a gene includes a full length nonmodified nucleic acid as well as modified nucleic acids (e.g., with nucleotide insertions, deletions, inversions, and/or substitutions) that encode a protein product functionally equivalent to that encoded by a nonmodified gene.

Another embodiment of the present invention is a biotin-producing cell containing at least one deregulated TLM-sensitive enzyme that is capable of enhancing biotin precursor production by the cell. As used herein, a TLM-sensitive enzyme is an enzyme that, prior to deregulation, is sensitive to (i.e., substantially inactivated or inhibited by) a concentration of TLM that substantially inhibits or reduces biotin production by *Escherichia coli*. A preferred TLM-sensitive enzyme of the present invention has the activity of a KAS (i.e., is a KAS or a functional equivalent thereof) that when deregulated is capable of enhancing production of biotin precursors by the cell. A preferred method to deregulate a TLM-sensitive enzyme is to transform the cell with a TLM-sensitive enzyme nucleic acid sequence, or functional equivalent of the sequence, the TLM-sensitive enzyme nucleic acid sequence being capable of encoding a TLM-sensitive enzyme, such that the enzyme, when deregulated is capable of enhancing biotin precursor production by a cell. Preferably, the cell is transformed with a KAS nucleic acid sequence, or functional equivalent thereof, the KAS nucleic acid sequence being capable of encoding a KAS enzyme, such that the enzyme, when deregulated, is capable of enhancing biotin precursor production by a cell.

A TLM-sensitive enzyme nucleic acid sequence of the present invention can be isolated in a variety of ways obvious to one skilled in the art, including the use of classical genetics (e.g., matings using Hfr [high frequency of recombination] strains) and/or recombinant DNA technology. For example, *Escherichia coli* cells transformed with a multicopy-number plasmid containing the entire *Escherichia coli* biotin operon operatively linked to a transcription control sequence are mutagenized and screened to obtain biotin auxotrophs. Using this technique, mutations in genes encoding enzymes of the biotin operon will likely not be detected since the genes on the multicopy number plasmid will complement any mutations in the cell's chromosomal biotin operon. Biotin auxotrophs obtained using this technique are likely to have mutations in genes involved in the production of pimelic acid, such as mutations in the bioH, accA, accB, accC, accD, and fabD genes as well as in the gene encoding the TLM-sensitive enzyme of the present invention. A cell having a mutation in a gene for which a clone of the gene is available can be identified by the ability of a plasmid containing that gene to complement a cell containing such a mutation. Remaining biotin auxotrophs, which include cells having mutations in the TLM-sensitive enzyme, can be used to identify and isolate the gene encoding the TLM-sensitive enzyme in the following manner. The auxotrophs can be transformed with an *Escherichia coli* genomic library and cells that can grow in the absence of biotin are selected. Plasmids contained within such cells are isolated and characterized (e.g., structurally, genetically, and biochemically) to identify a gene encoding a TLM-sensitive enzyme involved in biotin production, i.e., a TLM-sensitive nucleic acid sequence.

The inventors have made the surprising discovery that cellular biotin production is sensitive to TLM at a concentration that is less than or equivalent to about the concentration of TLM required to substantially inhibit (i.e., inactivate) *Escherichia coli* KAS I, KAS II, or KAS III. The inventors believe that neither KAS I nor KAS II are the primary enzymes involved in converting malonyl-ACP to the biotin precursor pimelyl-ACP, and that another TLM-sensitive enzyme, such as KAS III or another enzyme having 3-ketoacyl-ACP synthetase activity, is involved in controlling the flow of carbon from the fatty acid biosynthetic pathway into the biotin biosynthetic pathway. Genetic data, detailed in Example 1, suggest that neither KAS I nor KAS II are involved in biotin biosynthesis: *Escherichia coli* mutants having temperature sensitive mutations in either the fabB gene (encoding KAS I) or the fabF gene (encoding KAS II) do not require biotin supplementation in order to grow, whereas *Escherichia coli* mutants having temperature sensitive mutations in either the fabD gene (encodes MTA) or the accB gene (encodes BCCP) do require biotin supplementation in order to grow. The inventors have also demonstrated that cellular biotin production is essentially not sensitive to the antibiotic cerulenin (i.e., cerulenin does not substantially inhibit biotin production) even though both KAS I and KAS II are each inhibited by the concentration of cerulenin used in the experiment.

Yet another embodiment of the present invention is a biotin-producing cell containing at least one deregulated subunit of an acetyl coenzyme A carboxylase complex (ACC) or a functional equivalent thereof. ACC includes a deregulated biotin carboxylase (BC), or functional equivalent thereof; a deregulated biotin carboxyl carrier protein (BCCP), or functional equivalent thereof; and/or at least one deregulated carboxyltransferase (CT), or functional equivalent thereof. Preferably, at least one ACC subunit is deregulated by transforming a cell with at least one of the following ACC subunit nucleic acid sequences: a BC nucleic acid sequence, or functional equivalent thereof; a BCCP nucleic acid sequence, or functional equivalent thereof; and/or a CT nucleic acid sequence, or functional equivalent thereof. Preferred nucleic acid sequences with which to transform cells include an *Escherichia coli* accC gene, which encodes BC; an *Escherichia coli* accB gene, which encodes BCCP; an *Escherichia coli* accA gene, which encodes a subunit of CT; and an *Escherichia coli* accD gene, which encodes another subunit of CT; and mixtures thereof. In one embodiment, a cell of the present invention is transformed with *Escherichia coli* accA, accB, accC, and accD genes.

One embodiment of the present invention is a biotin-producing cell in which more than one enzyme of the fatty acid biosynthetic pathway is deregulated. Examples of such cells include (a) cells containing a deregulated MTA, or functional equivalent thereof; and a deregulated TLM-sensitive enzyme that, when deregulated, is capable of enhancing (i.e., increasing) biotin precursor production by the cell, the enzyme preferably having KAS activity; (b) cells containing a deregulated MTA, or functional equivalent thereof; and at least one deregulated ACC subunit, or functional equivalent thereof; (c) cells containing at least one deregulated ACC subunit, or functional equivalent thereof; and a deregulated TLM-sensitive enzyme that, when deregulated, is capable of enhancing biotin precursor production by the cell, the enzyme preferably having KAS activity; and (d) cells containing a deregulated MTA, or functional equivalent thereof; a deregulated TLM-sensitive enzyme that, when deregulated, is capable of enhancing biotin precursor production by the cell, the enzyme preferably having KAS activity; and at least one deregulated ACC subunit, or functional equivalent thereof. Deregulation of more than one enzyme can be accomplished in a variety of techniques, preferably by transformation of the cell with nucleic acids encoding the respective enzymes.

According to the present invention, a biotin-producing cell in which at least one enzyme selected from the group consisting of (a) MTA, (b) a deregulated TLM-sensitive enzyme that, when deregulated, is capable of enhancing biotin precursor production by the cell, the enzyme preferably having KAS activity, (c) at least one ACC subunit, (d) or functional equivalents of any of these enzymes is deregulated can also have at least one additional enzyme of the fatty acid biosynthetic pathway deregulated in order to permit more carbon to flow through the fatty acid biosynthetic pathway in order to enhance biotin precursor production. Additional deregulated fatty acid biosynthetic enzymes include, but are not limited to, a deregulated acyl carrier protein (ACP), a deregulated 3-ketoacyl-ACP reductase, a deregulated 3-hydroxyacyl-ACP dehydrase, a deregulated trans-2-acyl-ACP reductase, and functional equivalents of any of the enzymes. Preferably, such enzyme(s) in the cell are deregulated by transforming the cell with at least one of the following nucleic acid sequences: an ACP nucleic acid sequence, a 3-ketoacyl-ACP reductase nucleic acid sequence, a 3-hydroxyacyl-ACP dehydrase nucleic acid sequence, a trans-2-acyl-ACP reductase nucleic acid sequence, or functional equivalents of any of these sequences. Preferably, the ACP nucleic acid sequence is an *Escherichia coli* acpP gene.

Preferred cells of the present invention have a deregulated biotin biosynthetic pathway in addition to having at least one enzyme of the fatty acid biosynthetic pathway deregulated as heretofore described. While not being bound by theory, it is believed that deregulation of enzymes of the fatty acid biosynthetic pathway may lead to an accumulation of biotin precursors. Thus, a cell having a deregulated biotin pathway, in which conversion of biotin precursors to true biotin is not rate limiting, is a preferred cell of the present invention. Preferably at least about 25 percent, more preferably at least about 50 percent, even more preferably at least about 75 percent, and even more preferably at least about 90 percent of biotin precursors are converted to true biotin. Particularly preferred cells are able to convert essentially 100 percent of biotin precursors to biotin.

Cells having a deregulated biotin biosynthetic pathway have at least one protein (i.e., enzyme) of the biotin biosynthetic pathway that is deregulated. Preferred deregulated proteins include, but are not limited to, a deregulated protein encoded by an *Escherichia coli* bioA gene or a functionally equivalent protein (e.g., any protein having a biological activity similar to a deregulated diaminopelargonic acid aminotransferase); a deregulated protein encoded by an *Escherichia coli* bioB gene or a functionally equivalent protein (e.g., any protein having a biological activity similar to a deregulated biotin synthetase); a deregulated protein encoded by an *Escherichia coli* bioC gene or a functionally equivalent protein (e.g., any protein having a biological activity similar to a deregulated protein encoded by an *Escherichia coli* bioC gene); a deregulated protein encoded by an *Escherichia coli* bioD gene or a functionally equivalent protein (e.g., any protein having a biological activity similar to a deregulated protein encoded by an *Escherichia coli* bioD gene); a deregulated protein encoded by an *Escherichia coli* bioE gene or a functionally equivalent protein (e.g., any protein having a biological activity similar to a deregulated desthiobiotin synthetase); a deregulated protein encoded by an *Escherichia coli* bioF gene or a functionally equivalent protein (e.g., any protein having a biological activity similar to a deregulated ketoaminopelargonic acid synthetase); and a deregulated protein encoded by an *Escherichia coli* bioH gene or a functionally equivalent protein (e.g., any protein having a biological activity similar to a deregulated protein encoded by an *Escherichia coli* bioH gene).

A biotin biosynthetic pathway can be deregulated in a variety of ways, including the methods described for deregulating fatty acid biosynthetic pathway enzymes, such as derepressing synthesis of one or more proteins of the biotin biosynthetic pathway, increasing the specific activity of at least one such protein, amplifying the copy number of a nucleic acid sequence encoding such a protein, decreasing the activity of any enzymes competing for the same substrate, and combinations thereof. It is also within the scope of the invention that the parental cell has a deregulated biotin biosynthetic pathway.

A preferred method to deregulate the biotin biosynthetic pathway is to transform a cell with at least one nucleic acid sequence encoding at least one protein of the biotin biosynthetic pathway. Preferred nucleic acid sequences that encode proteins of the biotin biosynthetic pathway include, but are not limited to, an *Escherichia coli* bioA nucleic acid sequence or functional equivalent thereof; an *Escherichia coli* bioB nucleic acid sequence or functional equivalent thereof; an *Escherichia coli* bioC nucleic acid sequence or functional equivalent thereof; an *Escherichia coli* bioD nucleic acid sequence or functional equivalent thereof; an *Escherichia coli* bioE nucleic acid sequence or functional equivalent thereof; an *Escherichia coli* bioF nucleic acid sequence or functional equivalent thereof; and an *Escherichia coli* bioH nucleic acid sequence or functional equivalent thereof. As heretofore set forth, a functionally equivalent nucleic acid sequence is any nucleic acid sequence from any species that encodes a protein with substantially the same biological function as a protein encoded by the cited nucleic acid sequence. Thus, for example, a functional equivalent of an *Escherichia coli* bioA, bioB, bioD, or bioF nucleic acid sequence can be, respectively a *Bacillus sphaericus* bioA, bioB, bioD, or bioF nucleic acid sequence.

Preferred cells with deregulated biotin biosynthetic pathways include cells transformed with the following combinations of genes or functional equivalents thereof: (a) an *Escherichia coli* bioA gene, an *Escherichia coli* bioB gene, an *Escherichia coli* bioC gene, an *Escherichia coli* bioD gene, an *Escherichia coli* bioE gene, and an *Escherichia coli* bioF gene; (b) an *Escherichia coli* bioA gene, an *Escherichia coli* bioB gene, an *Escherichia coli* bioC gene, an *Escherichia coli* bioD gene, an *Escherichia coli* bioE gene, an *Escherichia coli* bioF gene, and an *Escherichia coli* bioH gene; and (c) a *Bacillus sphaericus* bioA gene, a *Bacillus sphaericus* bioB gene, an *Escherichia coli* bioC gene, a *Bacillus sphaericus* bioD gene, an *Escherichia coli* bioE gene, a *Bacillus sphaericus* bioF gene, and an *Escherichia coli* bioH gene.

One embodiment of the present invention is a method to produce a biotin-producing cell in which at least one enzyme of the fatty acid biosynthetic pathway is deregulated such that the cell is capable of enhanced production of biotin and/or biotin precursors. A variety of methods to deregulate such enzymes have been heretofore disclosed. A preferred method is to transform a host cell with at least one nucleic acid sequence encoding an enzyme of the fatty acid biosynthetic pathway in order to obtain a recombinant cell having enhanced biotin and/or biotin precursor production.

A host cell of the present invention is a parental cell that can be transformed. The host cell can be either an untransformed cell or a cell that is already transformed with a nucleic acid sequence, preferably a nucleic acid sequence encoding an enzyme of the fatty acid or biotin biosynthetic pathway. In addition, a host cell can already have at least one enzyme of the fatty acid or biotin biosynthetic pathway deregulated, for example, due to modifications within a gene on the host genome or to amplified gene copy number. Thus, the present invention can include transformation of a cell having a deregulated biotin biosynthetic pathway with an MTA nucleic acid sequence, such as an *Escherichia coli* fabD gene. Host cells of the present invention can either be indigenously (i.e., naturally) capable of biotin production or can be capable of producing biotin after being transformed with at least one nucleic acid sequence of the present invention.

Transformation can be accomplished using any process by which nucleic acid sequences are inserted into a cell. Transformation techniques include, but are not limited to, transfection, electroporation, microinjection, lipofection, adsorption, and protoplast fusion. A recombinant cell may remain unicellular or may grow into a tissue or a multicellular organism. Transformed nucleic acid sequences of the present invention can remain extrachromosomal or can integrate into one or more sites within a chromosome of a host cell in such a manner that their ability to be expressed is retained. Integrated nucleic acid sequences often are more stable than extrachromosomal sequences. As such, it is within the scope of the present invention that expression of nucleic acid sequences encoding enzymes involved in fatty acid and/or biotin biosynthesis may be due to expression of plasmid sequences or to sequences integrated into the host genome.

Nucleic acids of the present invention with which to transform cells include at least one nucleic acid sequence selected from the group consisting of (a) MTA nucleic acid sequences, (b) TLM-sensitive enzyme nucleic acid sequences (preferably KAS nucleic acid sequences), (c) ACC subunit nucleic acid sequences, or (d) functional equivalents thereof. Such cells can be further transformed with nucleic acid sequences encoding other enzymes of the fatty acid biosynthetic pathway and/or with nucleic acid sequences encoding enzymes of the biotin biosynthetic pathway. In a preferred embodiment, host cells are transformed with an MTA nucleic acid sequence (e.g., an *Escherichia coli* fabD gene) and at least one nucleic acid sequence that effectively deregulates the biotin biosynthetic pathway (e.g., the *Escherichia coli* biotin operon alone or in combination with an *Escherichia coli* bioH gene). In another embodiment, host cells are transformed with an MTA nucleic acid sequence (e.g., an *Escherichia coli* fabD gene), at least one TLM-sensitive nucleic acid sequence (preferably a KAS nucleic acid sequence), at least one ACC subunit nucleic acid sequence (e.g., an *Escherichia coli* accA, accB, accC, or accD gene, or mixtures thereof), and at least one nucleic acid sequence that effectively deregulates the biotin biosynthetic pathway (e.g., the *Escherichia coli* biotin operon alone or in combination with an *Escherichia coli* bioH gene).

Preferably, a recombinant cell is produced by transforming a host cell with one or more recombinant molecules, each containing one or more nucleic acid sequences of the present invention operatively linked to an expression vector containing one or more transcription control sequences. A cell can be transformed with one or more recombinant molecules. For example, in order to transform a cell with the *Escherichia coli* fabD gene and the *Escherichia coli* biotin operon, the cell can be transformed with: one recombinant molecule containing both the fabD gene and the biotin operon; with two recombinant molecules, one of which contains the fabD gene and the second of which contains the biotin operon; or with multiple recombinant molecules containing other combinations of the nucleic acid sequences.

As used herein, the phrase "operatively linked" refers to insertion of a nucleic acid sequence into an expression vector in a manner such that the sequence is able to be expressed when transformed into a host cell. As used herein, an expression vector is a DNA or RNA vector that is capable of transforming a host cell, of replicating within the host cell, and of effecting expression of a specified nucleic acid sequence. Expression vectors can be either prokaryotic or eukaryotic, and are typically viruses or plasmids. Expression vectors of the present invention include any vectors that direct gene expression in biotin-producing cells of the present invention, which can be of any species capable of producing fatty acids and biotin, including bacterial, yeast, other fungal, insect, animal, and plant cells. Preferred expression vectors of the present invention can direct gene expression in bacterial, yeast, and other fungal cells. More preferred expression vectors can direct gene expression in cells of the genus Escherichia, Bacillus, Pseudomonas, Salmonella, Corynebacterium, and/or Saccharomyces. Particularly preferred expression vectors are those that function (e.g., direct gene expression) in *Escherichia coli*, such as pDIP18, pKK223-3, pCKR101, AND pCE30.

Nucleic acid sequences of the present invention can be operatively linked to expression vectors containing regulatory sequences such as promoters, operators, repressors, enhancers, termination sequences, origins of replication, and other regulatory sequences that are compatible with the host cell and that control the expression of the nucleic acid sequences. In particular, expression vectors of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the host cells of the present invention and can include bacterial, yeast, other fungal, insect, animal, and plant transcription control sequences, Preferred transcription control sequences include, but are not limited to, any transcription control sequences that are able to control transcription in bacteria, yeast, and/or other fungi. More preferred transcription control sequences include those which function in Escherichia, Bacillus, Pseudomonas, Salmonella, Corynebacterium, and/or Saccharomyces. Even more preferred transcription control sequences include, but are not limited to, tac, lac, trp, trc, oxy-pro, bacteriophage lambda (such as lambda $p_L$ and lambda $p_R$), bacteriophage T7, bacteriophage T3, bacteriophage SP6, bacteriophage SP01, metallothionein (e.g., CUP1), alpha mating factor, and Pichia alcohol oxidase transcription control sequences. Even more preferred transcription control sequences are bacteriophage lambda $p_L$, bacteriophage lambda $p_R$, bacteriophage T7, and tac transcription control sequences. A preferred expression vector is pDIP18 (obtained from Dr. L. Gold, University of Colorado, Boulder, Colo.). pDIP18 contains a bacteriophage T7 transcription control sequencer which is recognized essentially only by bacteriophage T7 RNA polymerase. Other preferred expression vectors include pKK223-3 (available from Pharmacia, Piscataway, N.J.) and pCKR101 (Magnuson et al., ibid.), each of which contains a tac transcription control sequence regulated by the lac repressor. Thus, expression from these expression vectors can be induced by, for example, isopropyl-$\beta$-D-thiogalactoside (IPTG). Yet another preferred expression vector is pCE30 (Elvin et al., pp. 123–126, 1990, *Gene*, vol. 80), which contains both bacteriophage lambda $p_L$ and lambda $p_R$ transcription control sequences in an orientation such that the lambda $p_R$ transcription control sequence is inverted. Expression of nucleic acid sequences from this expression vector is controlled by the bacteriophage lambda repressor.

It is within the scope of the present invention that transcription control sequences can include both nucleic acid sequences, such as promoters, operators, and enhancers, as well as genes encoding RNA polymerases that recognize and initiate transcription from such signals, and genes encoding repressors that interact with the operators. For example, a bacteriophage T7 promoter and a gene encoding a bacteriophage T7 polymerase may be contained either on a plasmid or integrated into the host genome (for example, see Studier et al., pp. 113–130, 1986, *J. Mol. Biol.*, vol. 189). As an illustrative example, pDIP18, which contains a bacteriophage T7 promoter, can be transformed into a cell in which a gene encoding a bacteriophage T7 RNA polymerase operatively linked to an IPTG-inducible transcription control sequence has been integrated into the cell's chromosomal DNA.

Transcription control sequences of the present invention can include naturally occurring transcription control sequences previously associated with a nucleic acid sequence prior to isolation. For example, such transcription control sequences can include sequences associated with genes encoding enzymes involved in biotin or fatty acid biosynthesis. Biotin transcription control sequences, in particular, are usually subject to biotin regulation. Thus, such sequences are preferably used in cells in which biotin biosynthesis is deregulated (e.g., cells in which biotin production is no longer repressed by high concentrations of biotin, or by precursors or analogs thereof).

According to the present invention, nucleic acid sequences encoding one or more enzymes involved in biotin biosynthesis can be linked (a) individually, (b) as a group, or (c) as a combination thereof to transcription control sequences. The transcription control sequences can be identical or different for the different genes/nucleic acid sequences of the present invention. For example, all desired genes can be linked to a single transcription control sequence or some of the genes can be linked to one transcription control sequence and other genes to a second transcription control sequence.

A recombinant molecule of the present invention can be any nucleic acid sequence combination heretofore described operatively linked to any transcription control sequence capable of effectively regulating expression of the nucleic acid sequence in the cell to be transformed. Preferred recombinant molecules contain an MTA nucleic acid sequence, a TLM-sensitive enzyme nucleic acid sequence (preferably a KAS nucleic acid sequence), an ACC subunit nucleic acid sequence, functional equivalents thereof, or mixtures thereof. Such recombinant molecules can also include nucleic acid sequences encoding other enzymes of the fatty acid biosynthetic pathway and/or nucleic acid sequences encoding enzymes of the biotin biosynthetic pathway. Preferably, such nucleic acid sequences are operatively linked to at least one bacteriophage T7, bacteriophage lambda, or tac transcription control sequence. A particularly preferred recombinant molecule is pKM22, especially when it is used in conjunction with pDIPAEBFCD or pDIPHAEBFCD. Construction of pKM22, in which an *Escherichia coli* laDD gene has been operatively linked to pCKR101, is described in Magnuson et al., ibid. Construction of pDIPAEBFCD, in which the *Escherichia coli* bioA, bioE, bioB, bioF, bioC, and bioD genes are operatively linked to a T7 transcription control sequence, and of pDIPHAEBFCD, in which the *Escherichia coli* bioH, bioA, bioE, bioB, bioF, bioC, and bioD genes are operatively linked to a T7 transcription control sequence, is described by Eddy et al., ibid. Additional preferred recombinant molecules include pDIPbioAEBFCDfabD and pDIPbioHAEBFCDfabD in which the *Escherichia coli* fabD gene has been inserted into pDIPAEBFCD and pDIPHAEBFCD, respectively, in such a manner as to also be operatively linked to a T7 transcription control sequence.

Recombinant cells of the present invention include any cells transformed with any nucleic acid sequences of the present invention. Recombinant cells are preferably transformed with recombinant molecules containing an MTA nucleic acid sequence, a TLM-sensitive enzyme nucleic acid sequence (preferably a KAS nucleic acid sequence), an ACC subunit nucleic acid sequence functional equivalents thereof, or mixtures thereof. Such recombinant cells can also be co-transformed with recombinant molecules including nucleic acid sequences encoding other enzymes of the fatty acid biosynthetic pathway and/or nucleic acid sequences encoding enzymes of the biotin biosynthetic pathway. Alternatively, recombinant molecules containing an MTA nucleic acid sequence, a TLM-sensitive enzyme nucleic acid sequence (preferably a KAS nucleic acid sequence), an ACC subunit nucleic acid sequence functional equivalents thereof, or mixtures thereof, can also include nucleic acid sequences encoding other enzymes of the fatty acid biosynthetic pathway and/or nucleic acid sequences encoding enzymes of the biotin biosynthetic pathway. Preferred recombinant cells contain recombinant molecules having such nucleic acid sequences operatively linked to at least one bacteriophage T7, bacteriophage lambda, or tac transcription control sequence. Particularly preferred recombinant molecules with which to produce recombinant cells include pKM22, particularly when co-transformed with pDIPAEBFCD or with pDIPHAEBFCD. Additional particularly preferred recombinant molecules include pDIPbioAEBFCDfabD and pDIPbioHAEBFCDfabD. Particularly preferred recombinant cells include (a) *Escherichia coli* BL21/DE3—pKM22+pDIPAEBFCD (LU1818) and (b) *Escherichia coli* BL21/DE3—pKM22+pDIPHAEBFCD, which are *Escherichia coli* BL21/DE3 cells (see Studier et al., ibid.) co-transformed, respectively, (a) with recombinant molecules pKM22 and pDIPAEBFCD and (b) with recombinant molecules pKM22 and pDIPHAEBFCD. Additional preferred recombinant cells include *Escherichia coli* BL21/DE3—pDIPbioAEBFCDfabD and *Escherichia coli* BL21/DE3—pDIPbioHAEBFCDfabD, which are *Escherichia coli* BL21/DE3 cells co-transformed with recombinant molecule pDIPbioAEBFCDfabD and pDIPbioHAEBFCDfabD, respectively. The novel recombinant cell, *Escherichia coli* BL21/DE3—pKM22+pDIPAEBFCD (LU1818), identified above and discussed further below, was deposited under the Budapest Treaty on the International Recognition of the Deposit of Microorganisms for the Purposes of Patent Procedure with the DSM-DEUTSCHE SAMMLUNG VON MIKROORGANISMEN UND ZELLKULTUREN GmbH of Braunschweig, Germany, on Feb. 15, 1995, under the Accession No. DSM 9732.

It may be appreciated by one skilled in the art that use of recombinant DNA technologies can improve expression of transformed nucleic acid sequences by manipulating, for example, the number of copies of the nucleic acid sequences within a host cell, the efficiency with which those nucleic acid sequences are transcribed, the efficiency with which the resultant transcripts are translated, and the efficiency of post-translational modifications. Recombinant techniques useful for increasing the expression of nucleic acid sequences encoding enzymes involved in biotin synthesis include, but are not limited to, operatively linking nucleic acid sequences to high-copy number plasmids, integration of the nucleic acid sequences into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Delgarno sequences), modification of the nucleic acid sequences encoding enzymes involved in fatty acid and biotin biosynthesis to correspond to the codon usage of the host cell, deletion of sequences that destabilize transcripts, and use of control signals that temporally separate recombinant cell growth from recombinant enzyme production during fermentation. The activity of an expressed recombinant enzyme of the present invention may be improved by fragmenting, modifying, or derivatizing nucleic acid sequences encoding enzymes involved in biotin biosynthesis.

One embodiment of the present invention is the use of cells of the present invention in which at least one enzyme of the fatty acid biosynthetic pathway has been deregulated to produce biotin by culturing the cells in an effective medium and recovering biotin therefrom. As used herein, an "effective medium" refers to any medium in which a cell of the present invention, when cultured, is capable of producing biotin in desired amounts (i.e., detectably more biotin or biotin precursors than can a parental cell). An effective medium is typically an aqueous medium comprising assimilable carbohydrate, nitrogen and phosphate sources, as well as appropriate salts, minerals, metals and other nutrients, such as vitamins. The medium may comprise complex nutrients or may be a defined minimal medium. Cells of the present invention can be cultured in conventional fermentation bioreactors, which include, but are not limited to, batch, fed-batch, cell recycle, and continuous fermentors. Culturing is carried out at a temperature, pH and oxygen content appropriate for the recombinant cell. Such culturing conditions are well within the expertise of one of ordinary skill in the art. Examples of preferred effective media are included in the Examples section.

Preferred cells of the present invention are capable of producing at least about 10 mg, more preferably at least about 50 mg, and even more preferably at least about 200 mg, of biotin per liter of medium per day (i.e., within about 24 hours). It should be noted that the present invention does not depend on the total amount of biotin produced. That is, the present invention teaches a method to enhance biotin precursor and biotin production by deregulating fatty acid biosynthetic enzymes, particularly those involved in early steps of the pathway and, as such, is not limited by the amount of biotin produced.

Cells cultured in accordance with the present invention preferably produce primarily true biotin instead of biotin vitamers. It is recognized that, in at least some cases, the biotin biosynthetic pathway may need to be deregulated, using methods heretofore disclosed, in order to convert most of the biotin precursors, including biotin vitamers) into true biotin.

A preferred method to produce biotin in accordance with the present invention is a process including: transforming an *Escherichia coli* cell with at least *Escherichia coli* fabD, bioA, bioB, bioC, bioD, bioE, bioF, and bioH genes to form a recombinant cell; culturing the recombinant cell in a medium effective to produce biotin; and recovering biotin produced thereby.

As used herein, the term "recovering biotin" simply refers to collecting the whole fermentation medium comprising biotin and need not imply additional steps of separation or purification. Biotin can be further separated and/or purified from the fermentation medium using a variety of techniques known in the art. A simplified biotin purification method which results in high yields of essentially pure biotin is described in co-pending U.S. patent application Ser. No. 07/822,449, by Cheung, filed Jan. 17, 1992. Briefly, following fermentation, cells are separated from the biotin-containing supernatant by centrifugation or filtration. The supernatant is passed over an ion-exchange column from which the biotin is eluted using formic acid. This step effectively separates true biotin from biotin vitamers. Eluted fractions containing true biotin are acidified in order to precipitate the biotin, preferably by adjusting the pH of the eluent to a pH of from about pH 1 to about pH 4. The precipitated true biotin is subsequently dissolved and submitted to at least one step of crystallization.

The following examples are provided for the purposes of illustration and are not intended to limit the scope of the invention.

EXAMPLES

Example 1

Nutrition requirements of fatty acid auxotrophs

The following example demonstrates which fatty acid auxotrophs require fatty acid and/or biotin supplementation for growth. The data allow the identification of enzymes involved in both fatty acid and biotin biosynthesis and suggest the location of the branch by which carbon from the fatty acid biosynthetic pathway flows into the biotin biosynthetic pathway.

Several *Escherichia coli* fatty acid auxotrophs (available from the *Escherichia coli* Genetic Stock Center, New Haven, Conn.) having temperature sensitive mutations in one or more enzymes involved in fatty acid synthesis (as indicated in Table 1) were cultured under non-permissive conditions (i.e., about 42° C.) for about 16 hours in each of the following media: (a) Biotin-supplemented media, denoted "biotin" in Table 1, consisting of LB broth (10 g bacto-tryptone, 5 g bacto-yeast extract, and 10 g sodium chloride per liter of distilled water, adjusted to about pH 7.0); note that LB broth contains biotin. (b) Fatty acid supplemented media, denoted "fatty acid" in Table 1, consisting of LB broth; 1 unit/milliliter (U/ml) of avidin, which binds with high affinity to the biotin in LB broth, thereby "inactivating" the vitamin (i.e., the concentration of active biotin is at less than about 5 nanograms/ml); 0.01% oleate; and 0.01% palmitate. Growth was analyzed by measuring the optical density of the culture at 600 nanometers ($OD_{600}$). An $OD_{600}$ of at least about 1.0 was indicative of growth, whereas an $OD_{600}$ of less than about 0.1 was indicative of no growth. The results are shown in Table 1.

TABLE 1

Nutritional requirements of fatty acid auxotrophs

| Strain | fab allele | factors required for growth | |
|---|---|---|---|
| | | biotin | Fatty Acid |
| L8 | fabE22 | yes | yes |
| L48 | fabD89 | yes | yes |
| CY50 | fabA2 | no | yes |
| M5 | fabB15 | no | yes |
| CY288 | fabF200, fabB15 | no | yes |

This experiment indicates that Escherichia coli cells having either a temperature sensitive fabE (also known as accB) or fabD gene require both fatty acids and biotin in order to grow. In contrast, although Escherichia coli cells having a temperature sensitive fabA gene, fabB gene, or both fabB and fabF genes, require fatty acids for growth, such mutants do not require biotin to grow. These results strongly suggest that Escherichia coli accB and fabD genes are involved in biotin synthesis, whereas Escherichia coli fabA, fabB, and fabF genes are not. In other words, at least BCCP (encoded by accB) of the ACC complex and MTA (encoded by fabD) of the fatty acid biosynthetic pathway are apparently involved in the production of biotin precursors, whereas KAS I (encoded by fabB), KAS II (encoded by fabF), and 3-hydroxydecanol-ACP dehydrase (encoded by fabA) apparently are not involved in the production of biotin precursors.

Example 2

Sensitivity of biotin production to cerulenin

This example demonstrates that cerulenin, an antibiotic that inhibits KAS I and KAS II of the fatty acid biosynthetic pathway apparently does not inhibit biotin production. This example also shows that MTA is involved in fatty acid biosynthesis.

Escherichia coli L48, which contains a temperature sensitive fabD gene (see Example 1), was cultured in each of the following medium, as indicated in Table 2: (a) "core media (cm)", which consists of LB broth to which is added 1 U/ml avidin to "inactivate" biotin; (b) "cm+biotin", which consists of LB broth without avidin supplementation; (c) "cm+fatty acid", which consists of LB broth, 1 U/ml avidin, 0.01% oleate, and 0.01% palmitate; and (d) "cm+biotin+fatty acid", which consists of LB broth, 0.01% oleate, and 0.01% palmitate. Each of the media also contained 100 μg/ml cerulenin (available from Sigma, St. Louis, Mo.; stored as a 1 mg cerulenin per 1 ml DMSO solution at −20° C.). The cells were cultured at either about 32° C. (permissive temperature) or about 42° C. (nonpermissive temperature) for about 6 hours. Growth was analyzed by measuring the optical density of the culture at 600 nanometers ($OD_{600}$). The results are shown in Table 2.

TABLE 2

Effect of cerulenin on the growth of Escherichia coli fabD$^{ts}$ strain in various media at permissive and nonpermissive temperatures

| Media supplements | Growth at 32° C. | Growth at 42° C. |
|---|---|---|
| core medium (cm) | .028 | .019 |
| cm + biotin | .045 | .017 |
| cm + fatty acid | .280 | .054 |
| cm + biotin and fatty acid | .246 | .209 |

These results indicate that an Escherichia coli fabD$^{ts}$ strain must be fed both biotin and fatty acids to grow at the nonpermissive temperature, indicating that the fabD gene (which encodes MTA) is apparently involved in both fatty acid and biotin synthesis. The experiment also demonstrates that Escherichia coli fabD$^{ts}$ cells cultured at a permissive temperature in a medium containing cerulenin and fatty acids but lacking biotin are capable of growing, suggesting that KAS I and KAS II are not involved in biotin production.

Example 3

Sensitivity of biotin production to TLM

This example demonstrates that TLM, an antibiotic previously only thought to be associated with inhibition of fatty acid production, also inhibits biotin production.

Escherichia coli W3110 (a wild type strain having an inversion in the rrnD-rrnB region of the genome; available from the Escherichia coli Genetic Stock Center, New Haven, Conn.) cells was cultured in each of the following media either in the presence or absence of TLM, as indicated in Table 3: (a) "core media (cm)", which consists of LB broth to which is added 1 U/ml avidin to "inactivate" biotin; (b) "cm+biotin", which consists of LB broth without avidin supplementation; (c) "cm+fatty acid", which consists of LB broth, 1 U/ml avidin, 0.01% oleate, and 0.01% palmitate; and (d) "cm+biotin+fatty acid", which consists of LB broth, 0.01% oleate, and 0.01% palmitate. TLM was isolated by chloroform extraction of Nocardia sp. 2-200 by a modified method of Oishi et al., pp. 391–395, 1982, J. Antibiotics, vol. 35. Briefly, Nocardia sp. 2-200 was cultured as described by Oishi et al. The cell-containing broth was acidified to pH 3.5 with hydrochloric acid. An equal volume of methanol was added to the acidified broth. TLM was extracted with chloroform, and the chloroform fraction was used without further purification. An "inhibitory amount of TLM" was determined by culturing Escherichia coli cells in the presence of varying concentrations of TLM until a TLM concentration was found (i.e., an inhibitory amount) that inhibited cell growth. For the experiment, the results of which are presented in Table 3, cells were cultured at about 37° C. for about 60 hours after inoculation, at which point cell growth was analyzed by measuring the optical density of the culture at 600 nanometers ($OD_{600}$). The initial $OD_{600}$ (i.e., at inoculation) was less than 0.05.

TABLE 3

Effect of TLM on the growth of Escherichia coli W3110 in various media

| Medium | $OD_{600}$ with TLM | $OD_{600}$ without TLM |
|---|---|---|
| core medium (cm) | .085 | 1.910 |
| cm + biotin | .090 | 1.977 |
| cm + fatty acid | .101 | 1.856 |
| cm + biotin and fatty acid | 1.024 | 1.913 |

This experiment demonstrates that, although W3110 grew well in each of the media in the absence of TLM, W3110 could only grow in the presence of TLM when both biotin and fatty acids were added to the core medium. These results suggest that TLM inhibits the biosynthesis of biotin as well as of fatty acids. Since only enzymes with KAS activity are known to be inhibited by TLM, the results suggest that an enzyme having KAS activity is involved in the production of biotin precursors. Taken together, the results from Examples 1, 2, and 3 suggest that MTA, at least BCCP of the ACC complex, and a TLM-sensitive enzyme (likely having KAS activity) are involved in the production of biotin precursors, and hence biotin.

Example 4

Production of biotin by cells transformed with a *Escherichia coli* fabD gene and genes of the *Escherichia coli* biotin operon This Example shows that cells transformed with both the *Escherichia coli* fabD gene and *Escherichia coli* biotin operon produces significantly more biotin than do cells transformed with just the *Escherichia coli* biotin operon.

Figure 4A:
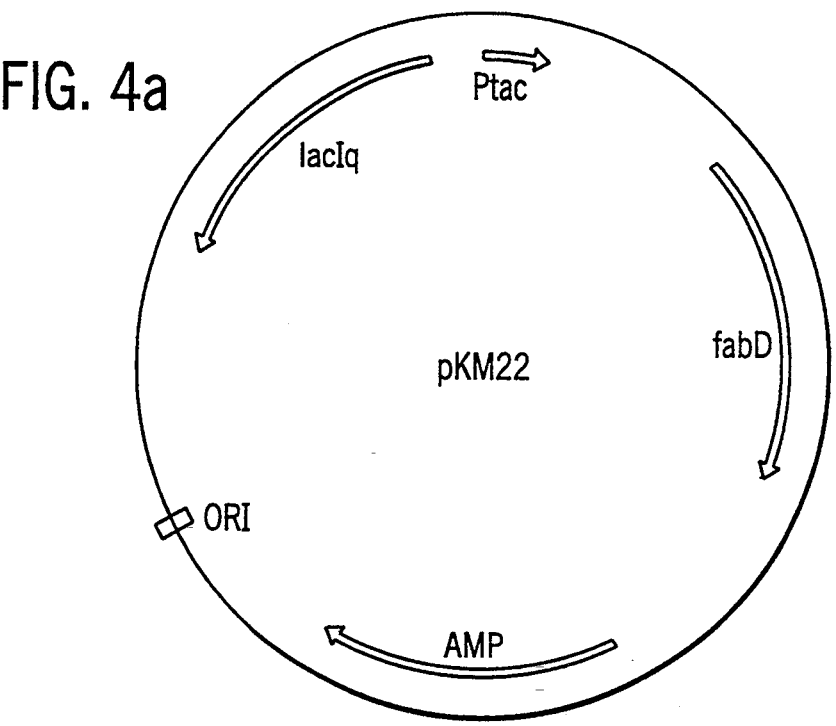
FIG. 4a is a schematic drawing of a recombinant molecule containing the *Escherichia coli* fabD gene.
Figure 4B:
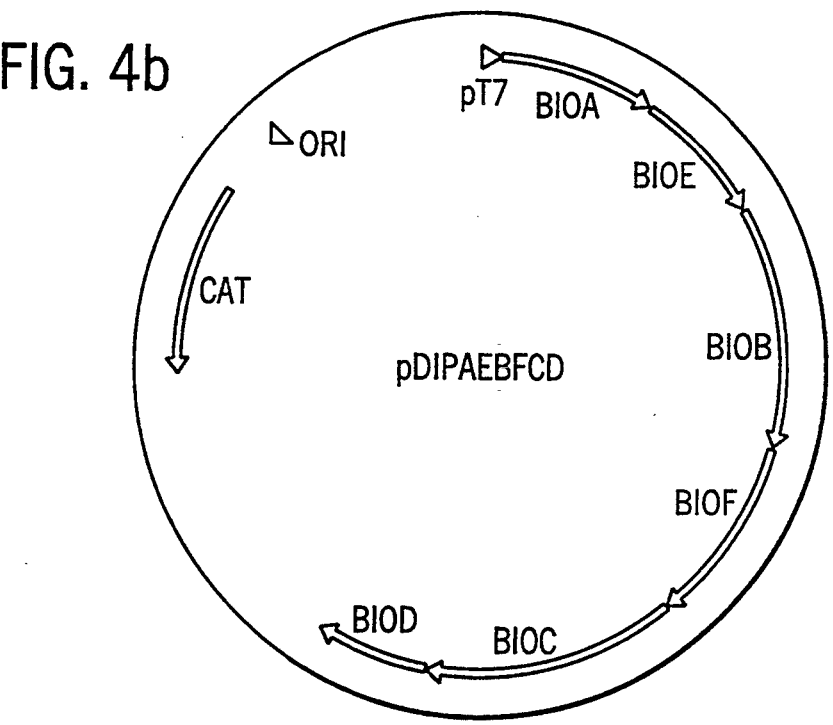
FIG. 4b is a schematic drawing of a plasmid containing several genes of the *Escherichia coli* biotin biosynthetic pathway.

A. Recombinant cell *Escherichia coli* BL21/DE3—pKM22+pDIPAEBFCD (LU1818) (Accession No. DSM 9732) was produced by co-transforming *Escherichia coli* BL21/DE3 cells: (Studier et al., ibid.) with recombinant molecule pKM22 (also denoted herein as pCKRfabD) and pDIPAEBFCD and selecting for cells capable of growing in medium containing about 75 μg/ml ampicillin and about 34 μg/ml chloramphenicol. pKM22 (Magnuson et al., ibid.) contains the *Escherichia coli* fabD gene operatively linked to a tac transcription control sequence, as shown in FIG. 4a. pDIPAEBFCD (Eddy et al., ibid.) contains *Escherichia coli* bioA, bioE, bioB, bioF, bioC, and bioD genes operatively linked to a bacteriophage T7 transcription control sequence, as shown in FIG. 4b.

B. *Escherichia coli* BL21/DE3—pCKR101+pDIPAEBFCD cells were produced by co-transforming *Escherichia coli* BL21/DE3 cells with pCKR101 (Magnuson et al., ibid.) and pDIPAEBFCD (see FIG. 4b) and selecting for cells capable of growing in medium containing about 75 μg/ml ampicillin and about 34 μg/ml chloramphenicol.

C. *Escherichia coli* BL21/DE3—pKM22+pDIPAEBFCD recombinant cells and *Escherichia coli* BL21/DE3—pCKR101+pDIPAEBFCD cells were cultured in shake flasks containing LB broth supplemented with about 75 μg/ml ampicillin and about 34 μg/ml chloramphenicol. When the cells reached an $OD_{600}$ of about 0.7 units in LB broth, each cultures was split into two flasks. In each case, IPTG was added to a final concentration of 0.5 mM IPTG in the first flask to induce expression of the genes operatively linked to pDIP-based and pCKR-based plasmids (i.e., "induced" cells). In the second flask, no IPTG was added (i.e., "uninduced" cells). Each of the four flasks of cells were cultured for an additional 3 hours, at which time samples were collected, filtered, and the supernatants measured for biotin content using a standard microbiological assay as described in Ogata et al., ibid. The results are shown in FIG. 5.

Figure 5:
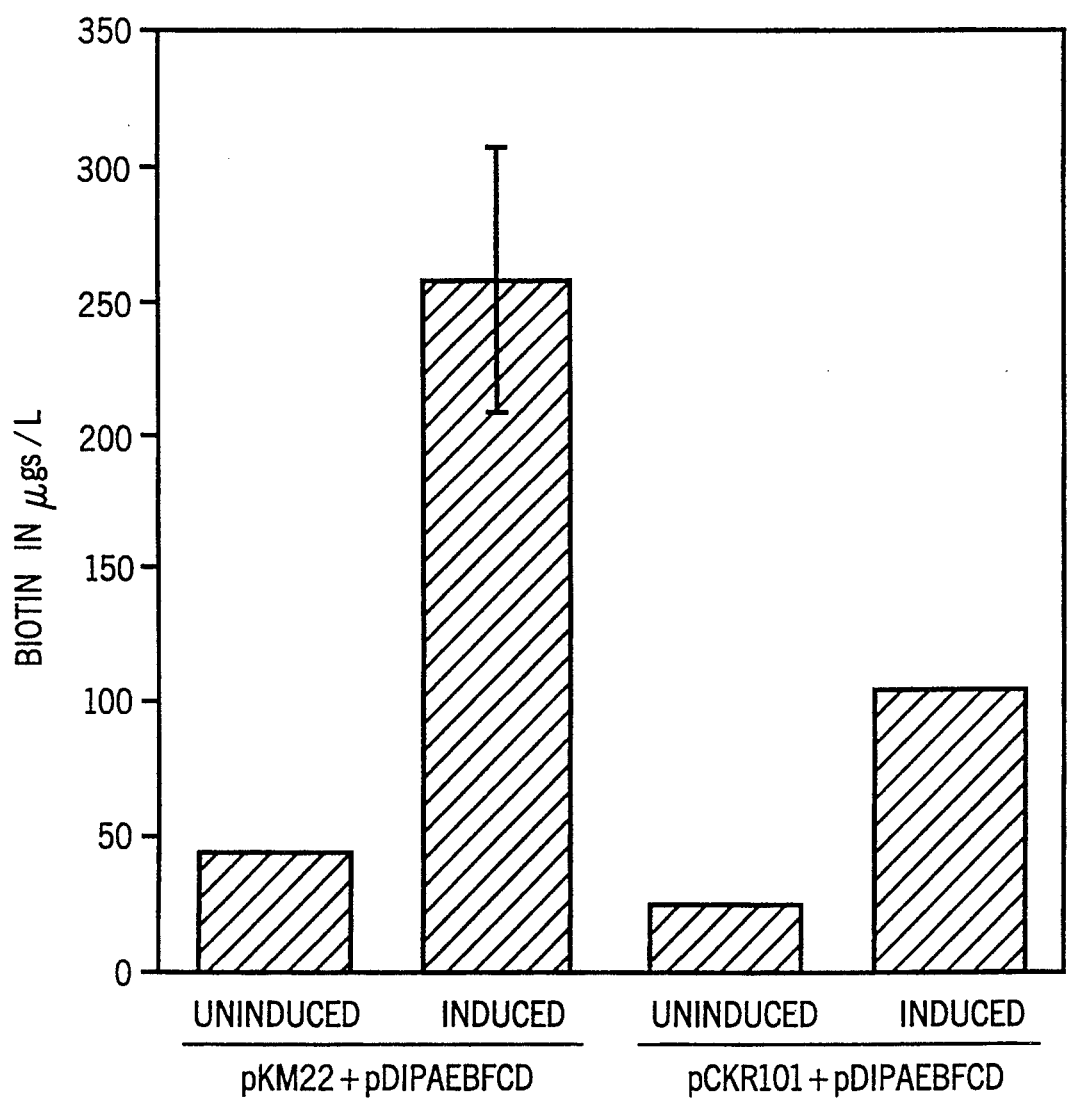
FIG. 5 is a graph comparing the amounts of biotin produced by cells transformed with the biotin operon with or without the *Escherichia coli* fabD gene.

*Escherichia coli* BL21/DE3—pKM22+pDIPAEBFCD (LU1818) (Accession No. DSM 9732) recombinant cells which were induced by IPTG (denoted in FIG. 5 as having the fabD allele and as being "induced") produced at least about 2.7 times as much biotin (as measured in μg biotin produced per liter of medium) as did IPTG-induced *Escherichia coli* BL21/DE3—pCKR101+pDIPAEBFCD cells (denoted in FIG. 5 as having no fab allele and as being "induced"). In addition, IPTG-induced *Escherichia coli* BL21/DE3—pKM22+pDIPAEBFCD (LU1818) (Accession No. DSM 9732) recombinant cells produced at least about 8.7 times as much biotin as did *Escherichia coli* BL21/DE3—pKM22+pDIPAEBFCD (LU1818) (Accession No. DSM 9732) cells which were not induced by IPTG (denoted in FIG. 5 as having a fabD allele but being "uninduced"). Both of these results indicate that amplification and enhanced expression of the *Escherichia coli* fabD gene enhances biotin production.

While various embodiments of the present invention have been described in detail, it is apparent that modifications and adaptations of those embodiments will occur to those skilled in the art. However, it is to be expressly understood that such modifications and adaptations are within the scope of the present invention, as set forth in the following claims.

What is claimed is:

1. A recombinant cell which is *Escherichia coli* BL21/DE3—pKM22+pDIPAEBFCD (LU1818).

2. A method to produce biotin comprising:
   (a) transforming an *Escherichia coli* cell with an *Escherichia coli* fabD gene, an *Escherichia coli* bioA gene, an *Escherichia coli* bioB gene, an *Escherichia coli* bioC gene, an *Escherichia coli* bioD gene, an *Escherichia coli* bioE gene, and an *Escherichia coli* bioF gene;
   (b) culturing said transformed cell in an effective medium; and
   (c) recovering biotin produced thereby.

3. The method of claim 2, further comprising transforming said cell with an *Escherichia coli* bioH gene.

* * * * *